United States Patent
Imran

(10) Patent No.: US 9,974,963 B2
(45) Date of Patent: *May 22, 2018

(54) APPARATUS AND METHOD FOR THE DETECTION AND TREATMENT OF ATRIAL FIBRILLATION

(71) Applicant: InCube Labs, LLC, San Jose, CA (US)

(72) Inventor: Mir A. Imran, Los Altos Hills, CA (US)

(73) Assignee: InCube Labs, LLC, San Jose, CA (US)

(*) Notice: Subject to any disclaimer, the term of this patent is extended or adjusted under 35 U.S.C. 154(b) by 20 days.

This patent is subject to a terminal disclaimer.

(21) Appl. No.: 14/812,247

(22) Filed: Jul. 29, 2015

(65) Prior Publication Data
US 2016/0022998 A1    Jan. 28, 2016

Related U.S. Application Data

(63) Continuation of application No. 14/224,900, filed on Mar. 25, 2014, now Pat. No. 9,138,160, which is a
(Continued)

(51) Int. Cl.
*A61N 1/00* (2006.01)
*A61N 1/365* (2006.01)
(Continued)

(52) U.S. Cl.
CPC .......... *A61N 1/36514* (2013.01); *A61B 5/046* (2013.01); *A61N 1/0573* (2013.01);
(Continued)

(58) Field of Classification Search
CPC ...... A61B 5/046; A61N 1/056; A61N 1/3621; A61N 1/3622; A61N 1/3624; A61N 1/3684; A61N 1/3702; A61N 1/395
See application file for complete search history.

(56) References Cited

U.S. PATENT DOCUMENTS 5,170,785 A   12/1992   Heinz et al.
5,181,511 A   1/1993    Nickolls et al.
(Continued)

FOREIGN PATENT DOCUMENTS

EP   0 830 876 A2   3/1998
JP   1994-27729     4/1994
(Continued)

OTHER PUBLICATIONS

International Search Report, Written Opinion and Notice of Transmittal of same dated Nov. 29, 2010 for PCT/US2010/031748.
(Continued)

*Primary Examiner* — Lindsey G Wehrheim
(74) *Attorney, Agent, or Firm* — Mahamedi IP Law LLP; Joel Harris

(57) ABSTRACT

Embodiments of the invention provide methods for detection and treatment of atrial fibrillation (AF) and related conditions. One embodiment provides a method comprising measuring electrical activity of the heart using electrodes arranged on the heart surface to define an area for detecting aberrant electrical activity (AEA) and then using the measured electrical activity (MEA) to detect foci of AEA causing AF. A pacing signal may then be sent to the foci to prevent AF onset. Atrial wall motion characteristics (WMC) may be sensed using an accelerometer placed on the heart and used with MEA to detect AF. The WMC may be used to monitor effectiveness of the pacing signal in preventing AF and/or returning the heart to normal sinus rhythm (NSR). Also, upon AF detection, a cardioversion signal may be sent to the atria using the electrodes to depolarize an atrial area causing AF and return the heart to NSR.

20 Claims, 8 Drawing Sheets

Related U.S. Application Data continuation of application No. 14/168,680, filed on Jan. 30, 2014, now Pat. No. 9,764,142, which is a continuation of application No. 12/757,865, filed on Apr. 9, 2010, now Pat. No. 8,731,662, which is a continuation of application No. 12/427,733, filed on Apr. 21, 2009, now Pat. No. 8,644,927.

(51) Int. Cl.
| | |
|---|---|
| A61N 1/362 | (2006.01) |
| A61N 1/368 | (2006.01) |
| A61N 1/39 | (2006.01) |
| A61B 5/046 | (2006.01) |
| A61N 1/05 | (2006.01) |
| A61N 1/37 | (2006.01) |

(52) U.S. Cl.
CPC ......... *A61N 1/3621* (2013.01); *A61N 1/3684* (2013.01); *A61N 1/36578* (2013.01); *A61N 1/395* (2013.01); *A61N 1/056* (2013.01); *A61N 1/3622* (2013.01); *A61N 1/3624* (2013.01); *A61N 1/3702* (2013.01)

(56) References Cited

U.S. PATENT DOCUMENTS

| | | | |
|---|---|---|---|
| 5,683,429 A | 11/1997 | Mehra | |
| 6,023,638 A | 2/2000 | Swanson | |
| 6,295,476 B1 | 9/2001 | Schaenzer | |
| 6,466,811 B1 | 10/2002 | Hassett | |
| 7,272,438 B2 | 9/2007 | Kroll et al. | |
| 7,308,310 B1 | 12/2007 | Levine et al. | |
| 8,644,927 B2* | 2/2014 | Imran .................. | A61N 1/3621 600/508 |
| 8,731,662 B2* | 5/2014 | Imran .................. | A61N 1/3621 600/508 |
| 9,138,160 B2* | 9/2015 | Imran .................. | A61N 1/3621 |
| 2003/0199956 A1 | 10/2003 | Struble et al. | |
| 2004/0019366 A1 | 1/2004 | Rottenberg et al. | |
| 2004/0215253 A1 | 10/2004 | Weinberg | |
| 2004/0225332 A1 | 11/2004 | Gebhardt et al. | |
| 2005/0090872 A1 | 4/2005 | Deno | |
| 2005/0288724 A1 | 12/2005 | Begemann et al. | |
| 2006/0149331 A1 | 7/2006 | Mann et al. | |
| 2006/0161211 A1 | 7/2006 | Thompson et al. | |
| 2006/0206157 A1 | 9/2006 | Hoijer | |
| 2007/0239248 A1 | 10/2007 | Hastings et al. | |
| 2008/0021505 A1 | 1/2008 | Hastings et al. | |
| 2008/0071338 A1 | 3/2008 | Jiang et al. | |
| 2008/0234773 A1 | 9/2008 | Ni et al. | |
| 2010/0076517 A1 | 3/2010 | Imran | |
| 2010/0268291 A1 | 10/2010 | Imran | |
| 2010/0268295 A1 | 10/2010 | Imran | |

FOREIGN PATENT DOCUMENTS

| | | |
|---|---|---|
| JP | 1995-000538 | 1/1995 |
| JP | 2003-529389 | 2/2000 |
| JP | 2007-500551 | 7/2004 |
| JP | 2007-500551 | 1/2007 |
| JP | 2000-502931 | 8/2008 |
| WO | WO 97/24983 A2 | 7/1997 |
| WO | WO 2002/087684 | 5/2003 |
| WO | WO 2007/115044 | 10/2007 |

OTHER PUBLICATIONS

Communication dated Sep. 11, 2012 in European Application No. 10767635.5.
Chinese Office Action dated Oct. 15, 2013 in CN Application No. 201080025213.
Examination Report in Australian Patent Application No. 2010239372, dated Jan. 13, 2014.
Office Action in Japanese Patent Application No. 2012-507312, dated Jan. 28, 2014.
Search Report dated Feb. 3, 2014 for European Application No. 13192236.1.
Second Office Action dated May 19, 2014 in CN Application No. 201080025213.
Intent to Grant dated Jul. 2, 2013 in European Application No. 10767635.5.
Communication dated Feb. 3, 2014 in European Application No. 13192236.1.

* cited by examiner

Normal Sinus Rhythm

Ventricular Signal During Atrial Fibrillation

Atrial Signal During Atrial Fibrillation

APPARATUS AND METHOD FOR THE DETECTION AND TREATMENT OF ATRIAL FIBRILLATION

RELATED APPLICATIONS

This application is a continuation of U.S. patent application Ser. No. 14/224,900, filed Mar. 25, 2014, which is a continuation of U.S. patent application Ser. No. 14/168,680, filed Jan. 30, 2014, which is a continuation of U.S. patent application Ser. No. 12/757,865, filed Apr. 9, 2010, now U.S. Pat. No. 8,731,662, issued on May 20, 2014, which is a continuation of U.S. patent application Ser. No. 12/427,733, filed Apr. 21, 2009, now U.S. Pat. No. 8,644,927, issued on Feb. 4, 2014. The aforementioned priority applications being hereby incorporated by reference in their entirety for all purposes.

FIELD OF THE INVENTION

Embodiments described herein relate to an apparatus and method for detection and treatment of atrial fibrillation. More specifically, embodiments described herein relate to an apparatus and method for detection and treatment of atrial fibrillation using distributed bipolar electrodes placed on the surface of the heart to detect the earliest onset of fibrillation.

BACKGROUND

The heart has four chambers, the right and left atria and the right and left ventricles. The atria serve as primer pumps to the ventricles which in turn pump blood to the lungs (the right ventricle) or the aorta and the remainder of the body (the left ventricle). The heart is essentially and electromechanical pump, which contracts and pumps blood by means of a wave of depolarization that spreads from the atria to the ventricles in a timed fashion through a series of conduction pathways. Cardiac arrhythmia is a condition afflicting the heart and is characterized by abnormal conduction patterns which in turn can affect the pumping efficiency in one of more chambers of the heart. It can occur in either the atria, ventricles or both. Particular types of Atrial arrhythmia can cause a condition known as atria fibrillation (AF) in which the pumping efficiency of the atria are compromised. Instead of contracting in a coordinated fashion, the left or right atria flutter with little or no pumping efficiency.

During an episode of AF, the normal electrical impulses that are generated by the sino-atrial node (the SA node), the natural pacemaker of the heart are overwhelmed by disorganized electrical impulses, known as ectopic foci that may originate in the atria or pulmonary veins, leading to conduction of irregular impulses to the atria and the ventricles. This can result in an irregular heartbeat, known as an arrhythmia which may occur in episodes lasting from minutes to weeks, or years. Left unchecked, AF often progresses to become a chronic condition.

Atrial fibrillation is often asymptomatic, and while not immediately life-threatening, may result in palpitations, fainting, chest pain (angina), or congestive heart failure. Patients with AF have a significantly increased risk of stroke and pulmonary embolism due to the tendency of blood to pool and form clots or emboli in the poorly contracting atria which are then sent to the lungs in the case of the right atria causing pulmonary embolism, or the brain causing stroke.

Atrial fibrillation may be treated with medications, implanted ventricular defibrillators or surgical procedures. The current medications used either slow the heart rate or revert the heart rhythm back to normal. However patients must remain on medication for life and many patients cannot be successfully treated with medication. Implanted ventricular defibrillators may be used to deliver a series of high voltage electric shocks to convert AF to a normal heart rhythm in a technique known as synchronized electrical cardioversion. However, these shocks are extremely painful and may cause the patient to pass or literally be knocked to the ground from the shock. Surgical and catheter-based therapies may also be used to ablate or destroy portions of the atria and pulmonary veins containing the ectopic and other foci responsible for the generation of arrhythmias causing AF; however these require open heart surgery, cardiac catheterization or both and have met with limited success. Thus, there is a need for improved methods and devices for the treatment of atrial fibrillation.

BRIEF DESCRIPTION

Embodiments of the invention provide apparatus, systems and methods for the detection and treatment of atrial fibrillation and related conditions. Many embodiments provide a system including a pacemaker coupled to endocardial and/or epicardial leads having a distributed pattern of bipolar electrodes for the early detection and treatment of atrial fibrillation.

In a first aspect, the invention provides an endocardial lead having multiple bipolar electrodes that attach to the endocardial surface of the right atria in a distributed pattern for the early detection and treatment of fibrillation in the right atria. Preferably, the electrodes are arranged in a circular or other pattern on the endocardial surface of the right atria to define an area for detecting the location of a foci of aberrant electrical activity causing onset (including earlier onset) of atrial fibrillation. In specific embodiments, the foci can be detected by an algorithm in the pacemaker which identifies the location on the endocardial surface (by the nearest electrode pair) having the earliest activation (i.e., depolarization) during an episode of AF.

Once a foci is detected, the electrodes nearest the foci can then be used to send a pacing signal at that site to prevent the site from causing atrial fibrillation. In some embodiments, that site of early activation can be paced continuously. The lead is coupled to a pacemaker to send sensed signals from each electrode pair back to the pacemaker electronics for analysis to determine the onset of atrial fibrillation or a signal predictive or the onset of atrial fibrillation. The lead can be positioned by in the right atria by introduction and advancement from the jugular vein using cardiac catheterization techniques known in the art.

In particular embodiments, the electrodes can be positioned in a circular, oval or related pattern around the SA node. The electrode pairs can be positioned on a circular or oval shaped patch that is attached to the endocardial surface using mechanical attachment element such as a helical screw, barbed needle or other attachment means such as a biocompatible adhesive. The adhesive can comprise a thermally activated adhesive that is activated by heat from the body or resistive heating from signals sent to the electrode pair. The patch can comprise a PTFE, polyester or other biocompatible material known in the art and is desirably configured to bend and flex with the motion of the heart wall. It may also include one or more nonthrombogenic coatings including coatings impregnated with various elutable drugs known in the art such as TAXOL to prevent thrombus, platelet and other cell adhesion. The electrodes can comprise a radio-opaque or echogenic material for visualizing a location of the electrodes in the heart under flouroscopy, ultrasound or other medical imaging modality. Also the patch can include a section made out of such materials to serves as a marker for visualizing the location of the electrodes in the heart.

In a related aspect, the invention provides an epicardial lead having multiple bipolar electrodes that attach to the epicardial surface of the left atria in a distributed pattern for the early detection and treatment of fibrillation in the left atria. Preferably, the electrodes are arranged in a pattern on the epicardial surface of the left atria to electrically map the atria so as detect the location of a foci of aberrant electrical activity causing early onset of atrial fibrillation in the left atria. The pattern includes placement of one or more electrodes adjacent one or more of the pulmonary veins so as to detect foci in these locations. Additionally, in left atria lead embodiments, the lead can also be coupled to a 3-axis accelerometer placed on the epicardial wall of the atria to sense atrial wall motion predictive of atrial fibrillation and normal sinus rhythm. The signal from the accelerometer may be used as a sole indication of AF, or it may be used to supplement the electrical signals from the bipolar leads positioned on the left atria to increase the predictive power of various algorithms used by the pacemaker for the detection of AF. Additionally, sensory inputs from the accelerometer can also be used to assess the effectiveness of atrial pacing signal in preventing AF and/or returning the heart to normal sinus rhythm.

In another aspect, the invention provides an apparatus, system and method for performing low voltage distributed cardioversion for converting the atria from a fibrillative state back to normal sinus rhythm. In these and related embodiments, the pacemaker can simultaneously send a higher voltage pacing signal (in the range of 8 to 10 volts) to all pairs of electrodes (e.g., on the particular atrial lead) to stimulate a large enough area of the atria to eliminate the arrhythmia. By using voltages lower than those typically used during external or internal cardioversion (which can be in the hundreds of volts for internal conversion to the thousands for external conversion) the pain experienced by the patient can be greatly reduced. The other benefit of this approach is that by using bipolar electrodes at each site, the electrical energy delivered to the heart can be contained in a very small region so that the risk of stimulating the ventricles (an unwanted effect in this case) is very small.

Further details of these and other embodiments and aspects of the invention are described more fully below, with reference to the attached drawing figures.

DETAILED DESCRIPTION OF THE INVENTION

Embodiments of the invention provide apparatus, systems and methods for the detection and treatment of atrial fibrillation and related conditions. Many embodiments provide a system including a pacemaker coupled to endocardial or epicardial leads having a distributed pattern of bipolar electrode for the early detection and treatment of atrial fibrillation.

Figure 1:
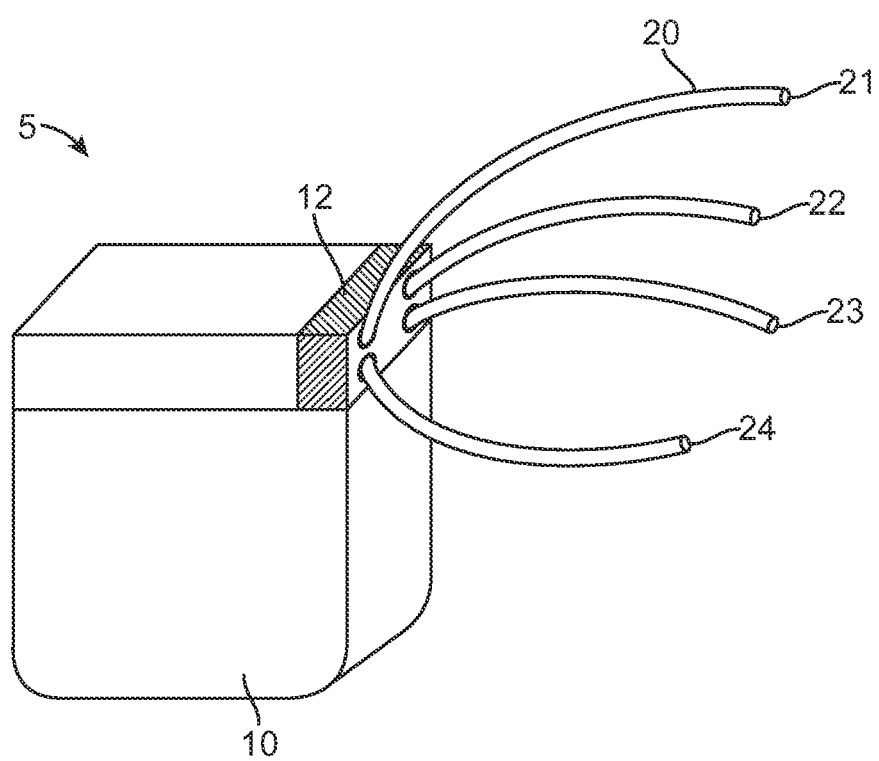
FIG. 1 is a lateral view showing an embodiment of a system for the treatment of atrial fibrillation including a pacemaker and various leads going to the atria and ventricles for AF detection and pacing and ventricular pacing.
Figure 2:
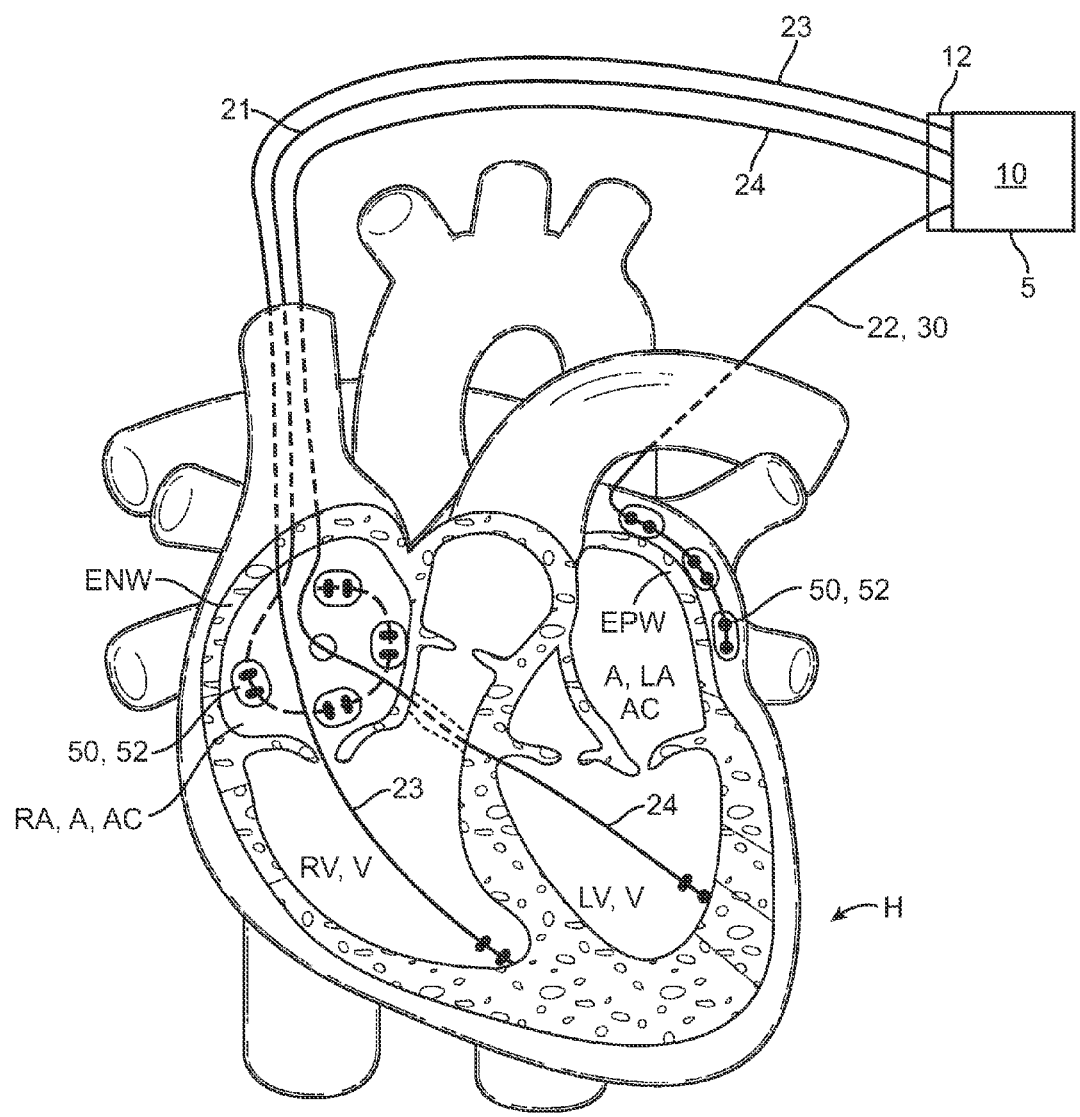
FIG. 2 is a cross sectional view of the heart showing the placement in the heart of the various leads from the embodiment of FIG. 1

Referring now to FIGS. 1-2, an embodiment of a system 5 for the detection and treatment of atrial fibrillation comprises a cardiac pace maker or related device 10, and one or more leads 20 positionable in/on the atria A and/or ventricles V of the heart H. Leads 20 can be coupled to pacemaker 10 by means of a multi-lead connector 12. In various embodiments, leads 20 can include: a lead 21 positionable on the endocardial wall ENW of the right atria RA for sensing and pacing the right atria; a lead 22 positionable on the epicardial wall EPW of the left atria LA for sensing and pacing the left atria, a lead 23 positionable on the endocardial wall of the right ventricle RV for sensing and pacing the right ventricle and a lead 24 positionable on the endocardial wall of the left ventricle LV for sensing and pacing the left ventricle.

Figure 3:
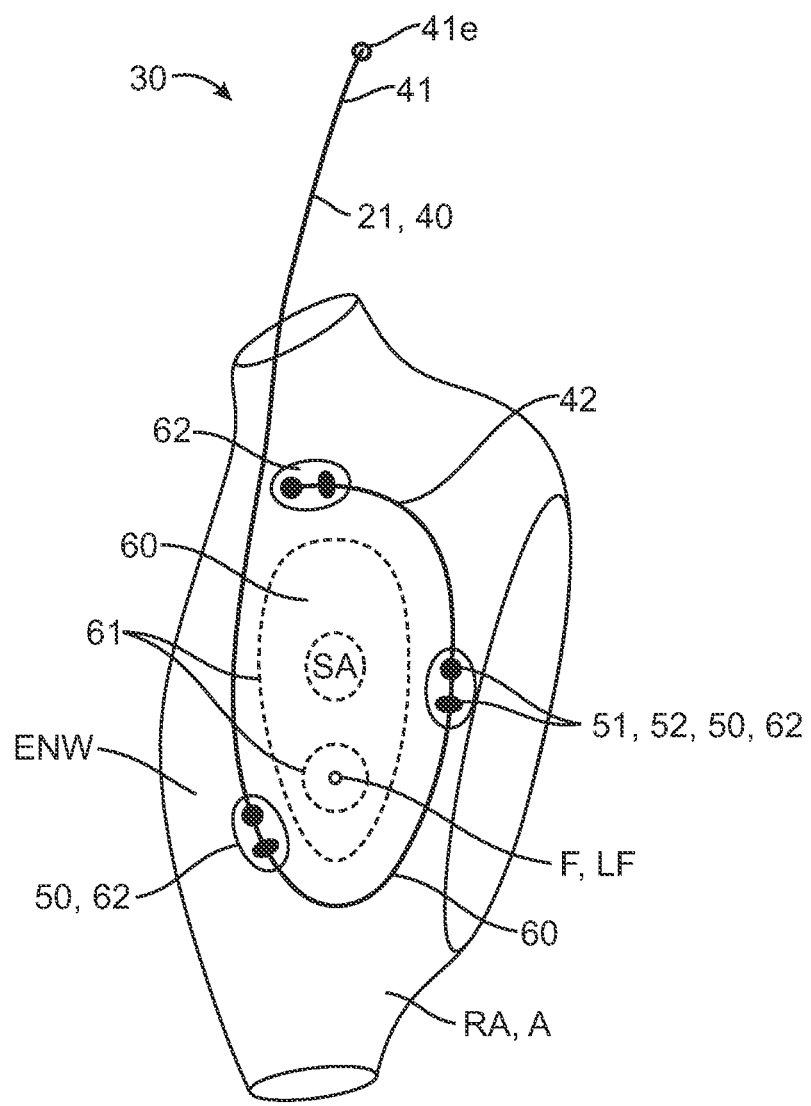
FIG. 3 is a side view of the right atria showing an embodiment of an atrial lead having a distributed pattern of bipolar electrodes placed on the endocardial surface of the right atria for the detection and treatment of AF.
Figure 4:
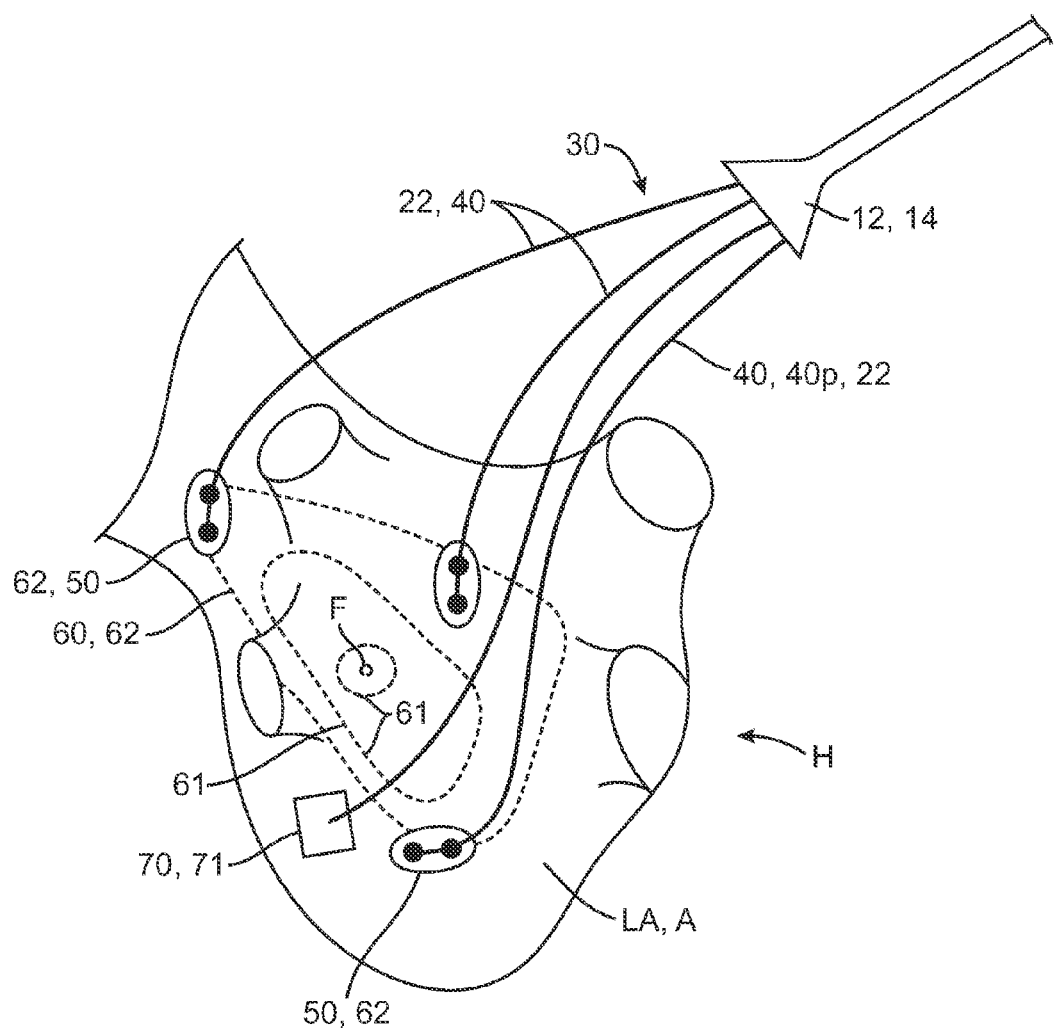
FIG. 4 is a side view of the left atria showing an embodiment of a parallel atrial lead configuration connected to a distributed pattern of bipolar electrodes placed on the epicardial surface of the left atria for the detection and treatment of AF.
Figure 5:
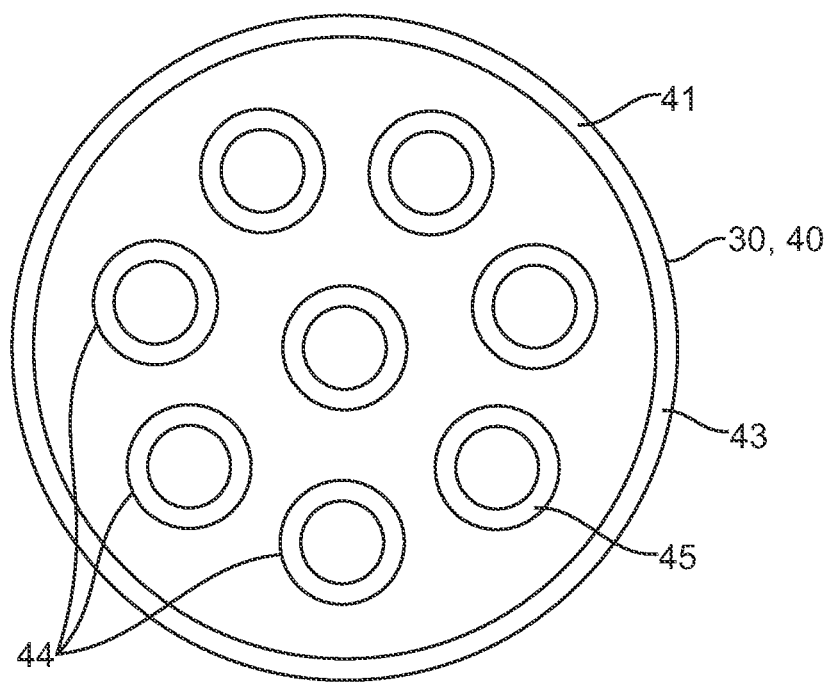
FIG. 5 is a cross sectional view showing an embodiment of an atrial lead for sensing and pacing.

Referring now to FIGS. 3-6, in various embodiments, leads 21 and/or 22 can comprise an apparatus 30 for the detection and treatment of atrial arrhythmia. Apparatus 30 can comprise a lead 40 having proximal and distal portions 41 and 42 and a plurality of electrode assemblies 50 coupled to the lead. As is described below, electrode assemblies 50 are distributed in a pattern 63 along lead 40 so as to define an area 60 for detecting and locating a foci of aberrant myoelectric activity causing atrial fibrillation. Apparatus 30 including lead(s) 40, can be configured for placement in various locations in the heart including the right atria RA, as is shown in the embodiment of FIG. 3, or the left atria LA, as is shown in the embodiment of FIG. 4. FIG. 4 also shows an embodiment of device 30 having a plurality 40p of leads 40 coupled in parallel to electrode assemblies 50 and pacemaker 10. In these and related embodiments leads 40 can be coupled to a common connector 14, which can be the same as connector 12.

The proximal portion of lead 40 includes an end 41e configured to be coupled to a pacemaker 10 or a related device. The distal portion 42 of the lead is configured to be positioned in an atrial chamber (right or left) AC of the heart H. Lead 40 comprises an outer sheath 43 surrounding a plurality of conductive wires 44 each having an insulative sheath 45 over all or a portion of their lengths. Conducive wires 44 can comprise copper or other conductive metal known in the art. Desirably, lead 40 also has sufficient flexibility and pushability as is known in the catheter arts to be advanced into the atrial chamber of the heart from a percutaneous introductory site such as the jugular vein in the neck or other like site.

In many embodiments, electrode assembly 50 comprises a pair 51 of bipolar electrodes 52 which are disposed in or otherwise positioned on a patch 53 or other support layer or structure 53 that can be attached to the heart wall. Electrode assembly 50 and electrodes 52 are configured to sense electrical activity within a region of myocardial tissue MT within the heart wall HW of the atria to detect an ectopic or other foci F of abnormal electric activity and send a pacing signal 56 to the heart wall to depolarize region MT containing the Foci F. Electrodes 52 are typically circular and can have diameters in the range of 1 to 10 mm with specific embodiment of 2, 5 and 7 mm, larger sizes are also contemplated. They can comprise various conductive metals known in the art including gold, platinum, silver, stainless steel and alloys thereof. They are desirably positioned on the tissue contacting surface 55 of assembly 50, but also may be recessed within the interior of the assembly so as to be capacitively coupled to the heart wall.

In preferred embodiments, the electrodes 52 of electrode assembly 50 are configured as bipolar electrodes. Such embodiments allow the depth of electrical energy delivered to myocardial tissue for purposes of pacing and cardioversion to be precisely controlled. However in alternative embodiments, electrodes 52 can be configured as monopolar electrodes with current flowing to a return electrode (not shown) positioned at another location on lead 40 or another lead 20.

Figure 6A:
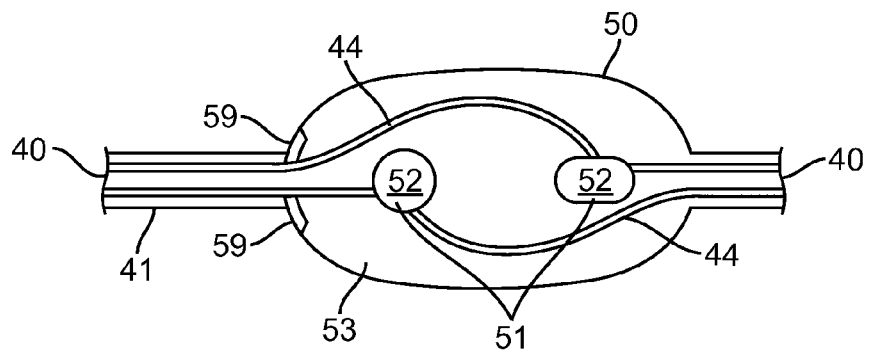
FIG. 6a is a top down view showing an embodiment of a bipolar electrode assembly including a pair of bipolar electrodes positioned on a patch or other support layer.
Figure 6B:
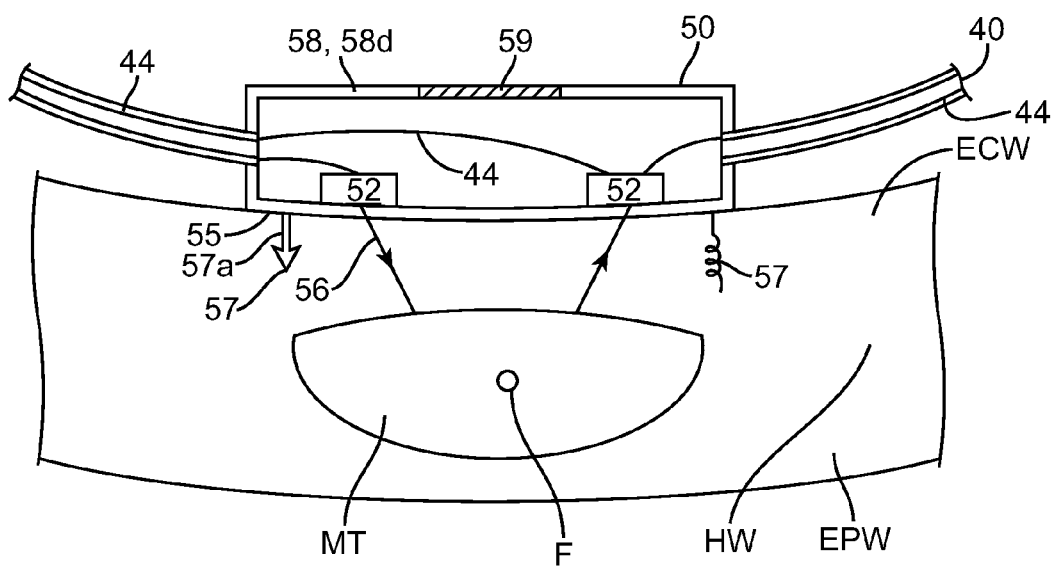
FIG. 6b is a cross sectional view showing positioning of an embodiment of the bipolar electrode assembly on the endocardial wall.

Electrode assembly 50 can be attached to the heart wall HW through several different means. According to an embodiment shown in FIG. 6b, the patch can include one or more attachment elements 57 that have tissue penetrating anchoring portions 57a which penetrate and anchor into the heart wall HW. Suitable attachment elements 57 can include various helical coils or barbed needles as is shown in FIG. 6b. Patch 53 may also be attached to the heart wall through use of biocompatible adhesives known in the art. In specific embodiments, the adhesive can comprise thermally activated adhesives that are activated by heat from flowing blood or electrical energy delivered from electrodes 52.

In various embodiments, lead 40 can include a plurality of electrode pairs 52/assemblies 50 which can be positioned in a distributed arrangement on the lead. In particular embodiments, the lead 40 can include between 2 to 10 pairs of electrodes with specific embodiments of 3, 4, 5, 6, 7 and 8 electrode pairs. Greater and lesser numbers of electrode pairs also contemplated depending upon the size and shape of atrial or ventricular chamber. The electrode pairs can be substantially equidistant from each with other spacing arrangements also contemplated. For example, particular spacing arrangements can be configured to account for the shape and size of a particular patient's atria which can be determined by prior imaging of the patient's heart. In specific embodiments, the spacing between electrode pairs 52 can be in the range from about 1 to about 5 cms with greater and lesser distances also contemplated.

Desirably, the spacing and number of electrodes pairs 52 on lead 40 or other lead are configured to allow the electrodes to sense the electrical activity (e.g., the amount and time course of depolarization) of a selected area 60 of myocardial tissue MT within the atria or ventricle. This in turn, allows for the generation of a conduction map 61 of tissue area 60. Conduction map 60 can be used to detect for the presence of one or more ectopic or other foci F of aberrant electrical activity within area 60.

In various embodiments, electrode pairs 52 can be arranged in a circular, oval or other distributed pattern 62 around a selected area 60 of the atrial or ventricular wall as is shown in the embodiments of FIGS. 3 and 4. In particular embodiments, electrode pairs 52/assemblies 50 are arranged in circular, oval or other pattern 62 around the SA node as is shown in the embodiment of FIG. 3 (desirably, the electrode pairs 52 are positioned to be substantially equidistant from the SA node). Such embodiments allow for the detection of particular foci F causing premature depolarization of the Atria by allowing comparison of the earliest depolarization within the entire area 60 (or adjacent to it) to that of the SA node. As is described herein, software algorithms resident 130 within pacemaker 10 can be used to detect the location LF of such foci F and then send a pacing signal to that location to take conductive control of the Foci and prevent it from causing AF.

In addition to electrodes 52, lead 40 can also include other sensors 70 for detection of various electrical and/or mechanical properties. In particular embodiments, sensors 70 can include an accelerometer 70, such as a 3 axis accelerometer for detection of atrial or other heart wall motion as is shown in the embodiment of FIG. 4. Similar to electrodes 52, sensors 70 be arranged in selectable distributed pattern 62 on the endocardial or epicardial surface of the heart, such as a circular, oval or other pattern.

Patch 53 will typically have an oval or other like shape, particularly for bipolar electrode embodiments, though other shapes are also contemplated. All or a portion of the patch can comprise various biocompatible polymers known in the art including PTFE, polyurethane, silicone and various other elastomers known in the. Desirably patch 53 has sufficient flexibility to conform to shape of heart wall as well as bend and flex with the motion of the heart so as to remain attached to the heart wall and not impede the motion of the heart wall. Patch 53 can also include one or more biocompatible non-thrombogenic coatings 58 such as silicone or other elastomeric coating. Coatings 58 can also have one more drugs 58d embedded in the coating, so as to be elutable over an extended period of time up to years. Drugs 58d can include various compounds such as Taxol or compound known in the stent arts for reducing platelet and cellular adhesion to the patch. Drugs 58d can also include various antibiotics and antimicrobials such as vancomyacin, cefamandol, gentamicin and silver compounds for reducing the likelihood of bacterial adhesion and growth, or infection of patch 53. In some embodiments, patch 53 can have a multilayer construction, in these and related embodiments, coating 58 can comprise a layer 58 which will typically be a tissue contacting layer 58.

In various embodiments, all or a portion of patch 53 and/or electrodes 52 can comprise a radio-opaque or echogenic material for visualizing a location of assembly 50 and/or electrodes 52 in the heart under flouroscopy, ultrasound or other medical imaging modality. Suitable radio-opaque materials include platinum and titanium dioxide. In particular embodiments, patch 53 can include a marker section 59 made out of such materials for visualizing the location of the electrode pair 51. Desirably, marker 59 is centrally located on the patch so as to be equidistant from each electrode 52, to enable the physician to use the marker as a guide for placing the electrodes at a desired location on the heart wall. Alternatively, marker 59 can be positioned on an edge of patch 53 as is shown in FIG. 6a.

In use, markers 59 allow for the precise placement of the electrode assemblies 50 along the endocardial wall of either the atria or the ventricles so as to define the selectable area 60 of the heart for measurement of electrical activity. For example, in particular embodiments the markers can be aligned with a superimposed image of an alignment template that marks the desired location for each electrode assembly. The markers also allow the physician to determine through various cardiovascular imaging methods that the electrode assemblies remain attached to heart wall over time. Additionally, once an ectopic or other foci F of aberrant electrical activity has been detected, they can be used as a point of reference for performing various RF ablative procedures to ablate the area of tissue responsible for the foci or otherwise create a conduction block around it.

Figure 7:
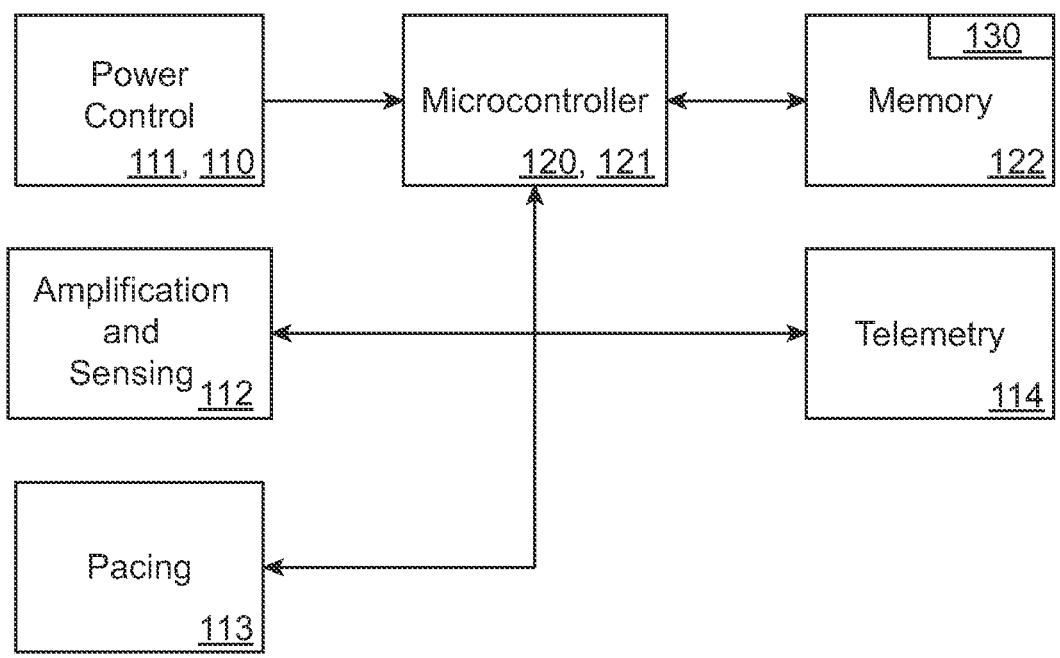
FIG. 7 is a block diagram illustrating some of the typical circuitry on a pacemaker or other implantable pacing or stimulating device.

Referring now to FIG. 7, pacemaker 10 can include various circuitry and other components. Some of the typical circuitry 110 and electronic devices 120 in a pacemaker 10 or like device can include power control circuitry 111, amplification and sensing circuitry 112, pacing circuitry 113, telemetry circuitry 114, micro-controller/micro-processor devices 121 and memory devices 122. One or more software algorithms 130 can be stored in memory device 122 and/or processor 121 for implementation by processor 121. Such algorithms 130 can include cardiac mapping and foci detection algorithms, pacing algorithms (both atrial and ventricular), atrial fibrillation detection algorithms, ventricular fibrillation detection algorithms, cardioversion algorithms (high and low voltage (e.g., 8 to 10 volts) and combinations thereof.

In embodiments of methods for positioning apparatus 30 in the body, the physician can place the endocardial lead in the right atrium by advancement from a percutaneous introductory site in the jugular vein or a related site. As described above, the desired positioning of the electrode assemblies 50 in the atria can be achieved by imaging the heart during placement and observing the position of markers 59. The epicardial leads can be placed using surgical techniques such as a mini-thorocotomy or a minimally invasive procedure using endoscopy. Additional leads can be positioned as needed in the right or left ventricles using minimally invasive or surgical techniques. One or more of these leads can be subsequently coupled to a pacemaker 10 positioned in the chest or other location.

Figure 8A:
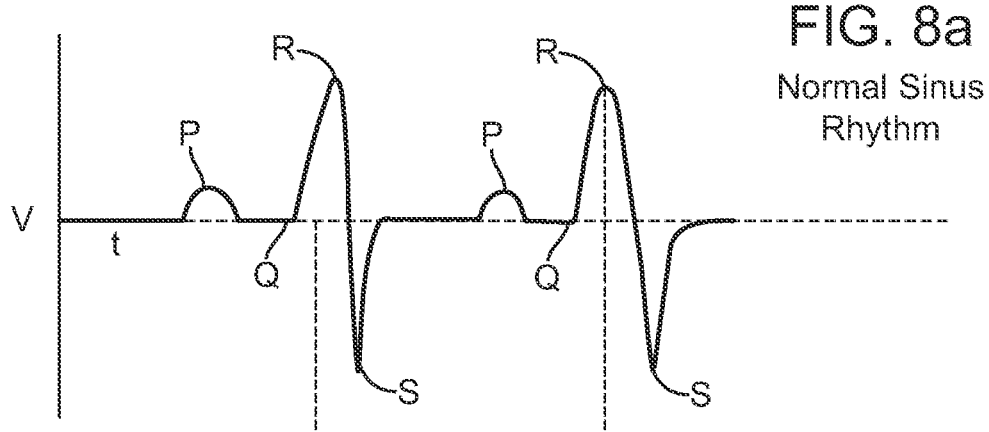
FIGS. 8a-8c are graphs showing an EKG for normal sinus rhythm (FIG. 8a) and during an episode of atrial fibrillation, including the ventricles (FIG. 8b) and atria (FIG. 8c).
Figure 8B:
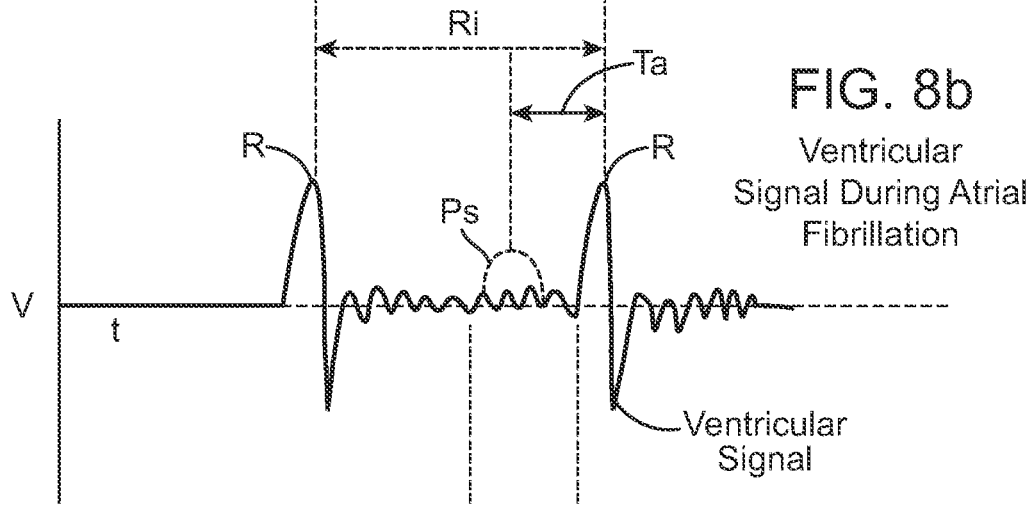
Figure 8C:
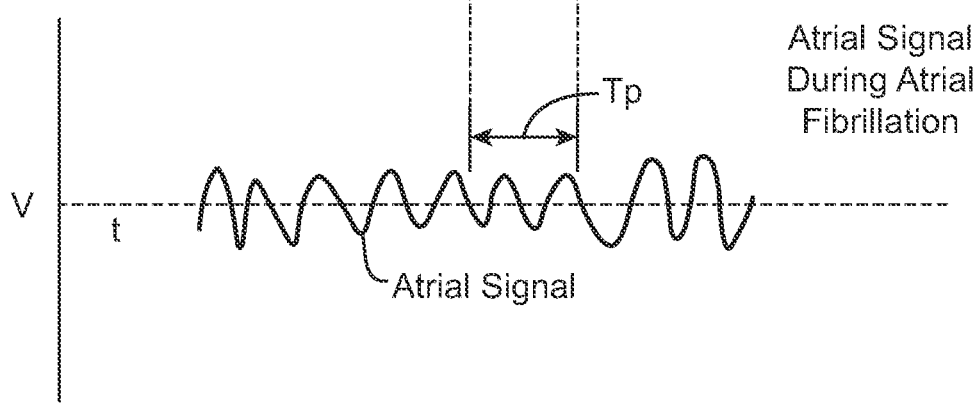

In exemplary embodiments of methods for using the invention, system 5 and atrially positioned leads 40 can be used to detect and treat atrial fibrillation in the following fashion. The distributed electrode assemblies can be used to monitor the patient's EKG including the P wave as well as map conduction in the area within or adjacent that circumscribed by the electrode assemblies, preferably this area includes the SA node. Atrial fibrillation can be detected based on the elimination or abnormality of the P wave as is shown in FIGS. 8b and 8c. When AF occurs, using the conduction map, the location of the ectopic or other foci causing the atrial fibrillation can be identified by looking at the time course of depolarization and identifying locations that depolarize before the SA node. Cardioversion can then be performed as described below to return the heart to normal sinus rhythm.

After cardioversion is performed and the heart returned to normal sinus rhythm, the electrode assemblies nearest that foci can then be used to send a pacing signal to that site and surrounding tissue to prevent the site from causing another episode of atrial fibrillation. Also, the location of that site can be stored in memory of the pacemaker so that next time abnormal atrial depolarization is detected, a pacing signal can be sent immediately to that site to prevent the occurrence of AF. In some embodiments, a site of early activation can be paced continuously. Atrial pacing can be performed to produce a stimulated P wave, $P_s$ which can be triggered off the R wave, R, or the R to R interval, $R_i$ as is shown in FIGS. 8a and 8b with appropriate time adjustment Ta for firing during the time period Tp when the normal P wave would be expected to occur.

In addition to detection of foci and other early activation/abnormal conductions sites in the atria, atrial fibrillation can also be detected using an accelerometer 71 such as a 3-axes accelerometer placed on the atrial wall (either epidcardial or endocardial) to sense atrial wall motion as is shown in the embodiment of FIG. 4. Such motion is predictive of atrial fibrillation via the effects atrial fibrillation has on atrial wall motion which typically flutter as a result. The signal from the accelerometer can be used to supplement the electrical signals from the bipolar leads positioned on the left atria to increase the predictive power of various algorithms used by the pacemaker for the detection of AF. Additionally, sensory inputs from the accelerometer can also be used to assess the effectiveness of atrial pacing signal in preventing AF and/or returning the heart to normal sinus rhythm.

As described above, when an episode of atrial fibrillation has been detected embodiments of the invention can also be used for performing cardioversion to convert the atria from a fibrillative state back to normal sinus rhythm. In these and related embodiments, the pacemaker can simultaneously send a higher voltage pacing signal (in the range of 8 to 10 volts) to all or majority of the pairs of distributed electrodes to simultaneously depolarize (also described herein as conductively capture) a large enough area of the atrial myocardium to stop the aberrant currents causing the atrial fibrillation. These voltages, while higher than those used for pacing to prevent AF, are much lower than those typically used during conventional internal cardio version (in the hundreds of volts) or external cardioverions (in the thousands of volts). Such lower voltages can be used because the stimulation is delivered by a multipoint source (resulting in higher current densities) and to a much smaller area of the heart than during typical internal or external cardioversion. By using voltages lower than those typically used during internal or external cardioversion, the pain experienced by the patient can be greatly reduced. The other benefit of this approach is that by using bipolar electrodes at each site, the electrical energy delivered to the heart can be contained to a relatively small region so that the risk of stimulating the ventricles (an unwanted effect in this case) is very small. The voltage level for achieving cardioversion can be adjusted based on one or more of the following factors (the "conversion voltage adjustment factors"): i) the size of the area of tissue bounded by distributed electrode pairs (smaller areas require less voltage); ii) the location of the ectopic foci (the closer the foci to a particular electrode pair the less the required voltage; iii) the number of foci (larger number of foci may require larger voltages); iv) the number of electrode pairs defining the area (the more electrodes the lower the voltage); and v) the number of prior episodes of AF (a larger number of episodes may require higher voltage). One or more of these factors can be programmed into the algorithm resident within the pacemaker which controls the cardioverion process. Also the conversion algorithm can programmed to use the lowest possible voltage at first, and then progressively increase it until conversion is achieved. The voltage which achieves conversion can then be stored in memory and used again as a starting point in a subsequent conversion attempt with tuning or fine tuning using one or more of the five conversion voltage adjustment factors described above.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus for detection and treatment of atrial arrhythmias and fibrillation can also be adapted for detection and treatment of various ventricular arrhythmias.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. An apparatus for detection and treatment of cardiac arrhythmia, the apparatus comprising:
   an electrical lead having a proximal and distal portion, the distal portion configured to be positioned in a chamber of a heart, the proximal portion having an end configured to be coupled to a pacemaker device, the electrical lead comprising a plurality of conductive wires;
   a plurality of membrane patches distributed along the electrical lead, each membrane patch configured to be attached to a wall of the heart and to bend and flex with motion of the heart without impeding motion of the heart; and
   a plurality of pairs of electrodes, wherein at least one pair of electrodes is positioned on each membrane patch, the electrodes of each pair being (i) coupled to a conductive wire of the electrical lead, and (ii) configured to at least sense an electrical signal of the wall of the heart; and
   wherein the distribution of the plurality of membrane patches and electrode pairs along the electrical lead is configured to allow the plurality of electrode pairs to be distributed in a pattern on the wall of the heart, the pattern configured to i) detect a location of a foci of aberrant electrical activity located within or adjacent to an area, and ii) send a pacing signal to that location to prevent or stop an occurrence of fibrillation caused by that foci.

2. The apparatus of claim 1, wherein the wall of the heart is an endocardial wall.

3. The apparatus of claim 1, wherein the electrical lead has a mechanical property configured to allow the electrical lead to be advanced to the chamber from a percutaneous introductory site.

4. The apparatus of claim 3, wherein the mechanical property is at least one of flexibility or pushability.

5. The apparatus of claim 1, wherein the plurality of electrode pairs include eight pairs of electrodes.

6. The apparatus of claim 1, wherein at least one of the electrode pairs includes a marker for visualizing a location of the electrode pair in the heart using a medical imaging modality.

7. The apparatus of claim 1, wherein the plurality of electrode pairs are configured and arranged in a pattern defining an area to send a simultaneous signal to the area from all of the electrode pairs to depolarize the area so as to convert a fibrillative state of the heart to normal sinus rhythm.

8. The apparatus of claim 1, wherein the pattern on the wall of the heart corresponds to a circular pattern.

9. The apparatus of claim 1, wherein the pattern on the wall of the heart corresponds to a pattern defining an area containing a sino-atrial (SA) node.

10. The apparatus of claim 9, wherein the pattern defining the area containing the sino-atrial (SA) node is arranged such that the electrode pairs are at selectable distances from the SA node so that the location of the foci of aberrant electrical activity can be determined relative to the SA node.

11. The apparatus of claim 9, wherein the pattern defining the area containing the sino-atrial (SA) node is arranged such that the electrode pairs are substantially equidistant from the SA node so that the location of the foci of aberrant electrical activity can be determined relative to the SA node.

12. The apparatus of claim 1, wherein the membrane comprises PTFE, silicone, polyurethane and/or polyester.

13. The apparatus of claim 1, wherein the membrane comprises an attachment element for attaching the membrane to the wall of the heart.

14. The apparatus of claim 13, wherein the attachment element comprises a barbed needle or a helical screw.

15. The apparatus of claim 1, wherein the chamber of the heart is a ventricular chamber.

16. The apparatus of claim 1, further comprising:
   an accelerometer coupled to at least one of the conductive wires, the accelerometer configured to be positioned on the wall of the heart and configured to sense motion of the wall of the heart.

17. The apparatus of claim 16, wherein the accelerometer is configured to sense motion in three axes.

18. A system configured to detect and treat cardiac arrhythmia, the system comprising:
   a pacemaker configured to be implanted; and
   the apparatus of claim 1, wherein at least one of the conductive wires is coupled to the pacemaker.

19. The system of claim 18, wherein the pacemaker includes a controller, the controller including an algorithm that utilizes the plurality of electrode pairs to detect an onset of fibrillation based on detection of a location of an earliest depolarization occurring before that from the sino-atrial node.

20. The system of claim 19, wherein the controller includes an algorithm configured to prevent the onset of fibrillation by sending a pacing signal to the location of the earliest depolarization.

* * * * *